United States Patent [19]
Santaniello et al.

[11] Patent Number: 6,080,786
[45] Date of Patent: Jun. 27, 2000

[54] SOLID COMPOSITIONS SUITABLE FOR ORAL ADMINISTRATION COMPRISING L-CARNITINE OR ALKANOYL-L-CARNITINE CHOLINE TARTRATE

[75] Inventors: Mosè Santaniello, Nettuno; Nazareno Scafetta, Pavona di Albano; Maria Ornella Tinti, Rome, all of Italy

[73] Assignee: Sigma-Tau Industrie Farmaceutiche Riunite S.p.A., Rome, Italy

[21] Appl. No.: 09/402,650

[22] PCT Filed: Apr. 4, 1998

[86] PCT No.: PCT/IT98/00080

§ 371 Date: Oct. 8, 1999

§ 102(e) Date: Oct. 8, 1999

[87] PCT Pub. No.: WO98/47857

PCT Pub. Date: Oct. 29, 1998

[30] Foreign Application Priority Data

Apr. 18, 1997 [IT] Italy ................................. RM97A0222

[51] Int. Cl.[7] ...................... C07C 229/22; A61K 31/205; A23L 1/30; A23K 1/16
[52] U.S. Cl. .......................... 514/547; 514/551; 514/556; 514/561; 560/196; 562/567
[58] Field of Search ...................................... 514/547, 551, 514/556, 561; 560/196; 562/567

[56] References Cited

U.S. PATENT DOCUMENTS

| 4,602,039 | 7/1986 | Carvazza . |
| 5,001,117 | 3/1991 | Hirsch . |
| 5,073,376 | 12/1991 | Kohl et al. . |

FOREIGN PATENT DOCUMENTS

| 0 402 755 | 12/1990 | European Pat. Off. . |
| 0 434 088 A1 | 6/1991 | European Pat. Off. . |
| 0 628 309 A1 | 12/1994 | European Pat. Off. . |
| 2 529 545 | 1/1984 | France . |
| 1153640 | 5/1969 | United Kingdom . |

*Primary Examiner*—Gary Geist
*Assistant Examiner*—Leigh C. Maier
*Attorney, Agent, or Firm*—Nixon & Vanderhye

[57] ABSTRACT

Stable and non-hygroscopic salts consisting of L-carnitine or alkanoyl-L-carnitine choline tartrate are disclosed. The salts are suitable for preparing solid compositions useful as dietary/nutritional supplements for human use and as fodder supplement for veterinary purposes.

12 Claims, No Drawings

SOLID COMPOSITIONS SUITABLE FOR ORAL ADMINISTRATION COMPRISING L-CARNITINE OR ALKANOYL-L-CARNITINE CHOLINE TARTRATE

This application is a §371 of PCT/IT98/0080, filed Apr. 18, 1997.

The present invention relates to stable, non-hygroscopic, pharmacologically acceptable salts of L-carnitine and lower alkanoyl-L-carnitines which favourably lend themselves to the preparation of solid, orally administrable compositions, which are useful not only as pharmaceuticals but also for the "health food" and "nutraceutical" market. The present invention also relates to such compositions.

Various therapeutic uses of L-carnitine and alkanoyl derivatives thereof are already known. For instance, L-carnitine has been used in the cardiovascular field for the treatment of acute and chronic myocardial ischaemia, angina pectoris, heart failure and cardiac arrhythmias.

In the nephrological field, L-carnitine has been administered to chronic uraemics undergoing regular haemodialytic treatment to combat myasthenia and the onset of muscular cramps.

Other therapeutic uses relate to the normalization of the HDL:LDL+VLDL ratio and total parenteral nutrition.

As regards the alkanoyl-L-carnitines, acetyl-L-carnitine has been used for the treatment of pathological disturbances of the CNS, particularly Alzheimer's disease and diabetic neuropathy; propionyl-L-carnitine has been used for treating peripheral vascular diseases and congestive heart failure.

It is also known that the salts of L(−)-carnitine and its alkanoyl derivatives present the same therapeutic or nutritional activities as those of the so-called inner salts and can, therefore, be used in their place, provided these salts are "pharmacologically acceptable", i.e. they do not present unwanted toxic or side effects.

In practice, then, the choice between an "inner salt" and a true L(−)-carnitine or alkanoyl-L(−)-carnitine salt will depend essentially on availability, economical and pharmacy considerations rather than on therapeutic or nutritional considerations.

The object of the present invention is to provide stable and non-hygroscopic salts of L-carnitine and lower alkanoyl-L-carnitines which are endowed with an enhanced therapeutical and/or nutritional efficacy with respect to their inner salt counterparts.

It should, therefore, be clearly understood that the utility of the salts of the present invention is not confined to their lack of hygroscopicity and higher stability compared to the corresponding inner salts, but also resides in their enhanced therapeutic and/or nutritional value. This value is, therefore, no longer to be attributed exclusively to the "carnitine" or "alkanoyl-L-carnitine" moiety of the salt. Therefore, although their lack of hygroscopicity allows these salts to be easily compounded, particularly with a view of preparing solid, orally administrable compositions, these salts are inherently useful also as "health foods" or "nutraceuticals".

As is well known to experts in pharmacy, the processing of hygroscopic products entails the use of controlled-humidity chambers both for storage and for the processing itself.

Moreover, the finished products must be packed in hermetically sealed blisters in order to avoid unpleasant consequences due to humidity.

All this involves extra costs both for the storage of raw materials and for their processing and packaging.

Among the populations of the industrialised countries there is an increasingly widespread use of nutritional or dietary supplements, "health foods" or "nutraceuticals" both by sportsmen (amateurs or professionals) and by people in good health.

The former use L-carnitine or nutritional/dietary supplements containing L-carnitine because it facilitates the oxidation of fatty acids and makes a larger amount of energy available to skeletal muscle, thus allowing enhanced performance and giving rise to less accumulation of lactic acid in the athletes' muscles.

People in good health use these nutritional supplements as health foods, i.e. for the purposes of favouring a reduction in serum fat levels and normalisation of the ratio between the various cholesterol fractions in order to prevent diseases related to lipid metabolism disorders.

It has been estimated that the amount of L-carnitine and its derivatives sold for non-ethical purposes is twice that sold for ethical purposes.

The US market for food supplements or nutraceuticals amounts to approximately 250 billion dollars, whereas the estimated figure for the European market is approximately 500 billion dollars (Food Labeling News, 1994, "Nutraceuticals" Market said to be a vast one, March, Vol. 2, n° 25; King Communications Group Inc., 1993, "Nutraceuticals" Foods, Drink in Global Market, Food and Drink Daily, April, Vol. 3, n° 503).

Some non-hygroscopic salts of L-carnitine are already known.

For instance EP 0 434 088 (LONZA) filed Dec. 21, 1990 discloses the use of the non-hygroscopic L(−)carnitine L(+) tartrare (2:1) (the preparation and physico-chemical characterization of which were, however, described by D. Müller and E. Strack in Hoppe Seyler's Z. Physiol. Chem 353, 618–622, April 1972) for the preparation of solid forms suitable for oral administration.

This salt presents, however, some drawbacks, such as e.g. the release, after prolonged storage, of traces of trimethylamine which give the product an unpleasant fishy odour. Moreover, L(−)-carnitine L(+)-tartrate (2:1) becomes deliquescent at relative humidity slightly exceeding 60%. Furthermore, L-(+)-tartaric acid is unable to give non-hygroscopic salts with the alkanoyl-L-carnitines, such as e.g. acetyl-L-carnitine. It should, furthermore, be noticed that tartaric anion is unable by itself to enhance the therapeutic/nutritional value of L-carnitine.

The aforesaid object of the present invention, i.e. to provide novel, pharmacologically acceptable salts of both L-carnitine and lower alkanoyl-L-carnitines which not only are stable and non-hygroscopic but also possess a higher therapeutic and/or nutritional value than the corresponding inner salts, is achieved by the salts of formula (I):

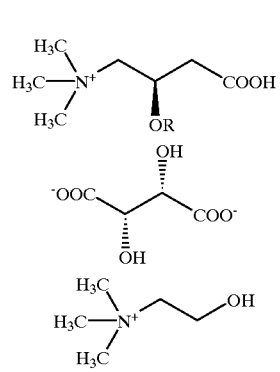

wherein R is hydrogen or a straight or branched lower alkanoyl having 2–5 carbon atoms.

Though choline, (β-hydroxyethyl trimethylammonium hydroxide, is extensively present in foods (e.g. egg yolk, liver, soya, wheat germs, peanuts, etc.) and is ingested mainly in the form of lecithin (phosphatidylcholine), recent studies have demonstrated that certain clinical and pathological conditions give rise to a deficiency of both choline and L-carnitine and that supplementation of the diet with these compounds is beneficial.

Choline chloride and bitartrate are mentioned in the US Code of Federal Regulations as nutrition/dietary supplements which have been accorded GRAS status (Generally Recognised As Safe).

They are, in fact, added to milk-based and nutritional products for infants (infant formulas) to ensure the presence of choline in an amount approximately equal to that present in fresh milk.

The US statutory regulations regarding nutritional products for infants (the 1980 Infant Formula Act) fix the choline chloride content at 7 mg per 100 calories as the required amount for such product when they do not contain milk as a basic constituent.

Choline, like L-carnitine inner salt, is a highly hygroscopic compound which, when it decomposes, emits an abnoxious fishy odour due to trimethylamine.

Choline acts as a source of methyl groups for the biosynthesis of other methylated products. It is the precursor of the neurotransmitter acetylcholine. It has been proved that the administration of choline is beneficial in patients suffering from any disorder related to defective cholinergic neurotransmission.

Choline is also a major component, along with lecithin, of phospholipids and sphingomyelin. By virtue of its fundamental functions in membrane structure, a choline deficiency causes a whole range of phospholipid abnormalities which express themselves clinically as fatty liver, kidney lesions (haemorrhagic renal necrosis) and impairment of lipoprotein metabolism. With a diet deficient in choline, cholesterol esters and fats accumulate in the liver.

On the other hand, however, it has recently been found that a supplementary choline intake leads to a reduction in the levels of L-carnitine and acyl L-carnitine in serum and urine in both sexes and that supplementation of the diet with exogenous L-carnitine enables normal levels to be restored.

There is no need to stress the importance of L-carnitine in the transport of acyl-CoA from the cytoplasm to the mitochondrial membrane where β-oxidation and energy production take place and that primary and secondary carnitine deficiencies are responsible for various diseases, ranging from a severe form of myopathy (type I lipid storage myopathy) to lipid metabolism disorders and disorders of the cardiovascular system.

The therapeutic uses of L-carnitine and of alkanoyl L-carnitine have, moreover, been previously mentioned.

The advantages obtainable with the salts of formula (I) are therefore evident:

(1) from the nutritional and theapeutic standpoints, they provide balanced amounts of both L-carnitine (or alkanoyl L-carnitine) and choline; and (2) from the point of view of pharmaceutical technology and industrial production processes, since these salts are stable, non-hygroscopic and devoid of the obnoxious odour of L-carnitine inner salt and choline, they facilitate the production and storage of the compositions containing them.

The following non-limiting example shows the preparation of a non-hygroscopic salt according to the present invention.

EXAMPLE

Preparation of L-carnitine choline L-(+)-tartrate (ST 1306)

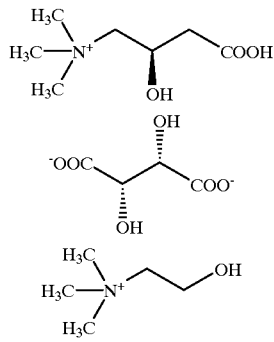

Choline hydrochloride (1.4 g; 0.01 moles) was dissolved in $H_2O$ and the resulting solution eluted on a strongly basic resin, AMBERLITE IRA 402 activated in $OH^-$ form. Equimolar amounts of L-carnitine inner salt (1.61 g; 0.01 moles) and L-(+)-tartaric acid (1.5 g; 0.01 moles) were added to the eluate.

The resulting mixture was kept under stirring at room temperature till complete dissolution was achieved and the solution was then concentrated under vacuum at 40° C.

The residue was first taken up with ethanol and then with acetone and the resulting mixture kept under stirring overnight and concentrated under vacuum. The pitchy residue thus obtained was added with acetone and the resulting mixture kept under stirring at 40° C. for 2 hours. By filtration, a solid non hygroscopic compound (3.5 g) was obtained.

$[\alpha]_D^{25} = +0.8 (c=1\%, H_2O)$

| Elementary analysis for $C_{16}H_{34}N_2O_{10}$ | | | |
|---|---|---|---|
| | C % | H % | N % |
| Calculated: | 46.36 | 8.27 | 6.76 |
| Found: | 46.16 | 8.41 | 6.51 |

NMR $D_2O$ δ; 4.5(1H,m,CHOH); 4.4(2H,s,2CHOH); 3.9 (2H,m,$CH_2OH$); 3,4(2H,t,$N^+CH_2CH_2$); 3.3(2H,m,$N^+CH_2$); 3.1–3.0(18H,2s,2($CH_3$)$_3N^+$); 2.4(2H,d,$CH_2COOH$)

| HPLC: | |
|---|---|
| Column: | Inertsil-ODS-3 (5 μm) 250 × 4.6 mm |
| Temperature: | 30° C. |
| Mobile phase: | $NaClO_4$ 0.15M + $NaH_2PO_4$ 0.05M pH = 2 with conc. $H_3PO_4$ |
| Flow rate: | 0.75 mL/min |
| L-(+)-tartaric acid: | $R_t$ = 3.58 min |
| Choline: | $R_t$ = 4.38 min |
| L-carnitine: | $R_t$ = 5.06 min |

The present invention also relates to compositions comprising as active principle(s) at least one of the aforesaid non-hygroscopic pharmacologically acceptable salts and, optionally, one or more pharmacologically acceptable excipients and active ingredients which are well-known to the experts in pharmacy and food technology.

Particularly preferred are the solid, orally administrable compositions such as tablets, chewable tablets and capsules, which comprise a salt of L-carnitine or alkanoyl-L-carnitine of formula (I) in an amount corresponding to 50–2,000 mg, preferably 100–1,000 mg, of L-carnitine or alkanoyl-L-carnitine inner salt.

For instance, a composition for preparing tablets is the following:

| | |
|---|---|
| Non-hygroscopic L-carnitine salt of formula (I) | 500 mg |
| Starch | 20 mg |
| Talc | 10 mg |
| Calcium stearate | 1 mg |
| | 531 mg |

A composition suitable for preparing capsules is the following:

| | |
|---|---|
| Non-hygroscopic L-carnitine salt of formula (I) | 500 mg |
| Starch | 20 mg |
| Lactose | 50 mg |
| Talc | 5 mg |
| Calcium stearate | 2 mg |
| | 577 mg |

The compositions of the present invention may be used as dietary/nutritional supplements for human use or as fodder supplement for veterinary purposes.

What is claimed is:

1. A salt of L-carnitine or alkanoyl-L-carnitine of formula (I)

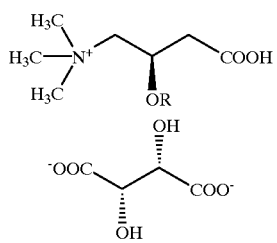

(I)

-continued

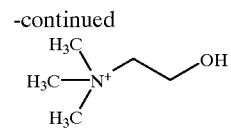

wherein R is hydrogen or a straight or branched lower alkanoyl having 2–5 carbon atoms.

2. The salt of claim 1, wherein R is selected from the group comprising acetyl, propionyl, butyryl, valeryl and isovaleryl.

3. L-carnitine choline tartrate.

4. Acetyl-L-carnitine choline tartrate.

5. Propionyl-L-carnitine choline tartrate.

6. A composition comprising as active ingredient the salt according to claim 1.

7. The composition of claim 6, further comprising one or more substances selected from pharmacologically acceptable excipients and active ingredients.

8. The composition of claim 6, in the form of tablets, chewable tablets, capsules, granulates or powders.

9. The composition of claim 6, in unit dosage form comprising as active ingredient the salt of L-carnitine or alkanoyl-L-carnitine of formula (I), in an amount corresponding to 50–2,000 mg, of L-carnitine or alkanoyl-L-carnitine inner salt.

10. The composition of claim 6 as dietary/nutritional supplement for human use.

11. The composition of claim 6 as fodder supplement for veterinary use.

12. The composition of claim 6, in unit dosage form comprising as active ingredient, the salt of L-carnitine or alkanoyl-L-carnitine of formula (I), in an amount corresponding to 100–1000 mg of L-carnitine or alkanoyl-L-carnitine inner salt.

* * * * *

UNITED STATES PATENT AND TRADEMARK OFFICE

CERTIFICATE OF CORRECTION

PATENT NO. : 6,080,786
DATED : June 27, 2000
INVENTOR(S) : SANTANIELLO et al

It is certified that error appears in the above-identified patent and that said letters patent is hereby corrected as shown below:

In the title page item [22] should read as follows:

--[22] PCT Filed: April 8, 2000--.

Signed and Sealed this

Twenty-fourth Day of April, 2001

Attest:

NICHOLAS P. GODICI

Attesting Officer

Acting Director of the United States Patent and Trademark Office